US011317861B2

(12) United States Patent
Ghajar et al.

(10) Patent No.: US 11,317,861 B2
(45) Date of Patent: May 3, 2022

(54) VESTIBULAR-OCULAR REFLEX TEST AND TRAINING SYSTEM (71) Applicant: Sync-Think, Inc., Boston, MA (US)

(72) Inventors: Jamshid Ghajar, Menlo Park, CA (US); Jun Maruta, New York, NY (US)

(73) Assignee: SYNC-THINK, INC., Palo Alto, CA (US)

( * ) Notice: Subject to any disclaimer, the term of this patent is extended or adjusted under 35 U.S.C. 154(b) by 769 days.

(21) Appl. No.: 15/585,057

(22) Filed: May 2, 2017

(65) Prior Publication Data
US 2017/0258397 A1 Sep. 14, 2017

Related U.S. Application Data (63) Continuation-in-part of application No. 14/454,662, filed on Aug. 7, 2014, now abandoned.
(Continued)

(51) Int. Cl.
A61B 3/113 (2006.01)
A61B 5/00 (2006.01)
(Continued)

(52) U.S. Cl.
CPC ............ A61B 5/486 (2013.01); A61B 3/0091 (2013.01); A61B 3/032 (2013.01); A61B 3/085 (2013.01);
(Continued)

(58) Field of Classification Search
CPC . A61B 3/11; A61B 3/111; A61B 3/113; A61B 3/08; A61B 3/085; A61B 3/032; A61B 5/165
(Continued)

(56) References Cited

U.S. PATENT DOCUMENTS 4,332,566 A 6/1982 Mazeski et al.
4,407,299 A 10/1983 Culver
(Continued)

FOREIGN PATENT DOCUMENTS

EP 1726260 11/2006
EP 2095759 A1 9/2009
GB 2496005 1/2013

OTHER PUBLICATIONS

Weber, K. P., et al. "Head impulse test in unilateral vestibular loss: vestibulo-ocular reflex and catch-up saccades." Neurology 70.6 (2008): 454-463. (Year: 2008).*
(Continued)

Primary Examiner — David J. McCrosky
(74) Attorney, Agent, or Firm — Morgan, Lewis & Bockius LLP (57) ABSTRACT A system and method for testing a subject for cognitive or oculomotor impairment includes presenting the subject with a display of an object, while presenting the display to the subject, and the subject's head moves horizontally or vertically within a predefined range of movement rates, measuring the subject's right eye positions and/or the subject's left eye positions. The system generates a metric by statistical analysis of the measurements of subject's right eye positions or the subject's left eye positions, and generates a report based on the metric. In some embodiments, the system is configured to train the subject to improve their performance, and thereby remediate or reduce cognitive and oculomotor impairment.

9 Claims, 6 Drawing Sheets

Related U.S. Application Data (60) Provisional application No. 62/330,757, filed on May 2, 2016, provisional application No. 61/865,546, filed on Aug. 13, 2013.

(51) Int. Cl.

| | | |
|---|---|---|
| G09B 19/00 | (2006.01) | |
| A61B 3/00 | (2006.01) | |
| A61B 5/16 | (2006.01) | |
| A61B 3/032 | (2006.01) | |
| A61B 3/08 | (2006.01) | |
| A61B 3/11 | (2006.01) | |
| G16H 15/00 | (2018.01) | |

(52) U.S. Cl.
CPC .............. *A61B 3/111* (2013.01); *A61B 3/113* (2013.01); *A61B 5/165* (2013.01); *A61B 5/168* (2013.01); *A61B 5/4088* (2013.01); *G09B 19/003* (2013.01); *G16H 15/00* (2018.01)

(58) Field of Classification Search
USPC .......................................... 351/209; 600/558
See application file for complete search history.

(56) References Cited

U.S. PATENT DOCUMENTS

| | | | |
|---|---|---|---|
| 4,838,681 A | 6/1989 | Pavlidis | |
| 4,885,687 A | 12/1989 | Carey | |
| 4,889,422 A | 12/1989 | Pavlidis | |
| 5,070,883 A | 12/1991 | Kasahara | |
| 5,137,027 A | 8/1992 | Rosenfeld | |
| 5,331,969 A | 7/1994 | Silberstein | |
| 5,491,492 A | 2/1996 | Knapp et al. | |
| 5,529,498 A | 6/1996 | Cassily et al. | |
| 5,583,795 A * | 12/1996 | Smyth ................ | A61B 3/0025 359/630 |
| 5,649,061 A | 7/1997 | Smyth | |
| 5,662,117 A | 9/1997 | Bittman | |
| 5,743,744 A | 4/1998 | Cassily et al. | |
| 5,867,587 A | 2/1999 | Aboutalib et al. | |
| 5,942,954 A | 8/1999 | Galiana et al. | |
| 6,090,051 A | 7/2000 | Marshall | |
| 6,102,870 A | 8/2000 | Edwards | |
| 6,162,186 A | 12/2000 | Scinto et al. | |
| 6,231,187 B1 | 5/2001 | Munoz et al. | |
| 6,542,081 B2 | 4/2003 | Torch | |
| 6,575,902 B1 | 6/2003 | Burton | |
| 6,603,491 B2 | 8/2003 | Lemelson et al. | |
| 7,280,678 B2 * | 10/2007 | Haven ................. | A61B 5/163 382/117 |
| 7,384,399 B2 | 6/2008 | Ghajar | |
| 7,390,091 B2 | 6/2008 | Clemons et al. | |
| 7,500,752 B2 * | 3/2009 | Nashner .............. | A61B 3/0091 351/210 |
| 7,819,818 B2 | 10/2010 | Ghajar | |
| 8,866,809 B2 | 10/2014 | McCarthy | |
| 9,072,481 B2 | 7/2015 | Shelhamer | |
| 9,078,598 B2 | 7/2015 | French et al. | |
| 10,258,259 B1 * | 4/2019 | Zets ..................... | A61H 5/00 |
| 2002/0099305 A1 | 7/2002 | Fukishima | |
| 2003/0225342 A1 | 12/2003 | Hong et al. | |
| 2005/0177065 A1 | 8/2005 | Ghajar | |
| 2006/0270945 A1 | 11/2006 | Ghajar | |
| 2007/0017534 A1 | 1/2007 | Thorpe | |
| 2007/0236663 A1 | 10/2007 | Waldorf et al. | |
| 2009/0115965 A1 | 5/2009 | Waldorf et al. | |
| 2010/0094161 A1 | 4/2010 | Kiderman et al. | |
| 2010/0167246 A1 | 7/2010 | Ghajar | |
| 2010/0280372 A1 | 11/2010 | Poolman | |
| 2010/0292545 A1 | 11/2010 | Berka | |
| 2013/0230252 A1 | 9/2013 | Hung | |
| 2013/0230253 A1 | 9/2013 | Stankiewicz | |
| 2013/0233097 A1 | 9/2013 | Hayner | |
| 2013/0300654 A1 | 11/2013 | Seki | |
| 2014/0154651 A1 | 6/2014 | Stack | |
| 2014/0255888 A1 | 9/2014 | Stack | |
| 2014/0313488 A1 | 10/2014 | Kiderman et al. | |
| 2014/0327880 A1 | 11/2014 | Kiderman et al. | |
| 2014/0330159 A1 | 11/2014 | Costa et al. | |
| 2015/0051508 A1 | 2/2015 | Ghajar et al. | |
| 2015/0062534 A1 | 3/2015 | Massengill | |
| 2015/0077543 A1 | 3/2015 | Kerr | |
| 2015/0097826 A1 | 4/2015 | McCarthy | |
| 2015/0130703 A1 * | 5/2015 | Ghajar ................ | G06F 3/013 345/156 |
| 2015/0141865 A1 | 5/2015 | Nakajima et al. | |
| 2015/0277710 A1 | 10/2015 | Lee et al. | |
| 2016/0022137 A1 | 1/2016 | Wetzel et al. | |
| 2016/0106315 A1 | 4/2016 | Kempinski | |
| 2016/0132726 A1 | 5/2016 | Kempinski et al. | |
| 2016/0299505 A1 | 10/2016 | Ohara | |
| 2016/0371726 A1 | 12/2016 | Yamaji et al. | |
| 2016/0379261 A1 | 12/2016 | Avalos et al. | |
| 2017/0123492 A1 | 5/2017 | Marggraff et al. | |
| 2018/0115673 A1 | 4/2018 | Yamasaki et al. | |
| 2018/0133504 A1 | 5/2018 | Malchano et al. | |
| 2018/0196511 A1 | 7/2018 | Chae | |
| 2018/0210546 A1 | 7/2018 | Rawlinson et al. | |

OTHER PUBLICATIONS

Hasegawa, Tatsuhisa, et al. "Active linear head motion improves dynamic visual acuity in pursuing a high-speed moving object." Experimental brain research 194.4 (2009): 505-516. (Year: 2009).*
Bronstein, Adolfo M., Mitesh Patel, and Qadeer Arshad. "A brief review of the clinical anatomy of the vestibular-ocular connections—how much do we know?." Eye 29.2 (2015): 163-170. (Year: 2015).*
Micromedical Technologies, Vorteq, Pamphlet. Printed Mar. 2014. (Year: 2014).*
"Eye Tracking," downloaded from http://en.wikipedia.org/wiki/eye_tracking, on Jun. 27, 2008, 5 pgs.
Glenstrup et al., "2 Present-day Eye-Gaze Tracking Techniques," downloaded from http://www.diku.dk/~panic/eyegaze/node8.html on Jun. 27, 2008, 3 pgs.
"Jonny Chung Lee>Projects>Wii," downloaded from http://www.cs.cmu.edu/~johnny/projects/wii/ on Jun. 28, 2008, 2 pgs.
Jonny Chung Lee, "Procrastineering giving into productive distractions," downloaded from http://procrastineering.blogspot.com/2007/12/wiimote.desktopvr~faq . . . , 4 pgs.
Kim et al., "Vision-Based Eye-Gaze Tracking for Human Computer Interface," 0-7803-5731-0/99, 1999 IEEE, pp. 324-329.
Kumar, Manu, "Gaze-enhanced User Interface Design," downloaded from http://hci.stanford.edu.reasearch/GUIDe/on Jun. 27, 2008, 2 pgs.
"The Exploratorium: seeing/seeing in context," downloaded from http://www.exploratorium.edu/seeing/about/seeing_attention.html on Jun. 28, 2008, 2 pgs.
Ball, The role of higher-order motor areas in voluntary movement as revealed by high-resolution EEG and fMRI.
Barnes, Anticipatory control of hand and eye movements in humans during oculo-manual tracking.
Chan, Are there sub-types of attentional deficits in patients with persisting post-concussive symptoms? A cluster analytical study.
Cronin-Golomb, et al., "Visual dysfunction in Alzheimer's disease: relation to normal aging," Annals of neurology 29.1 (1991): 41-52.
EPO OA, 06813639.9, May 31, 2011.
Gibbon, Toward a neurobiology of temporal cognition: advances and challenges.
Gredeback, The development of two-dimensional tracking: a longitudinal study of circular pursuit.
Green, Deficits in facial emotion perception in adults with recent traumatic brain injury.
Hulsmann, From will to action: sequential cerebellar contributions to voluntary movement.
ISR, PCT/US2006/032773, Jan. 22, 2007.

(56) References Cited

OTHER PUBLICATIONS

Kathmann, Deficits in gain of smooth pursuit eye movements in schizophrenia and affective disorder patients and their unaffected relatives.

Lane, D.M., "Measures of Variability," Online Stat Book, Internet Archive, Dec. 27, 2012, retrieved from <http://web-beta.archive.org/web/20121227105126/http://onlinestatbook.com/2/summarizing_distributions/variability.html> on Mar. 28, 2017, 4 pgs.

Lewine, Neuromagnetic assessment of pathophysiologic brain activity induced by minor head trauma.

Lutz, Guiding the study of brain dynamics by using first-person data: synchrony patterns correlate with ongoing conscious states during a simple visual task.

Madelain, Effects of learning on smooth pursuit during transient disappearance of a visual target.

Mangels, Effects of divided attention on episodic memory in chronic traumatic brain injury: a function of severity and strategy.

Mehta, Forward models in visuomotor control.

Pedersen, Origin of human motor readiness field linked to left middle frontal gyrus by MEG and PET.

Perbal, Relationships between time estimation, memory, attention, and processing speed in patients with severe traumatic brain injury.

Smith, A right hemispheric frontocerebellar network for time discrimination of several hundreds of milliseconds.

Strauss, Intraindividual variability in cognitive performance in three groups of older adults: cross-domain links to physical status and self-perceived affect and beliefs.

Sync-Think, Inc., International Search Report and Written Opinion, PCT/US2014/050774, dated Nov. 12, 2014, 13pgs.

Sync-Think, Inc., International Preliminary Report on Patentability, PCT/US2014/050774, dated Feb. 16, 2016, 9pgs.

Sync-Think, Inc., International Search Report, PCT/US2016/027923, dated Jul. 7, 2016, 13 pgs.

Sync-Think, Inc., International Preliminary Report on Patentability, PCT/US2016/027923, dated Oct. 17, 2017, 9 pgs.

Sync-Think, Inc., Communication Pursuant to Rules 161(1) and 162, EP14755513.0, dated Mar. 23, 2016, 2 pgs.

Sync-Think, Inc., Communication Pursuant to Article 94(3), EP14755513.0, dated Mar. 1, 2017, 5 pgs.

Squeri, Valentina et al., "Force-field compensation in a manual tracking task," PLoS One Jun. 2010, vol. 5, No. 6, e11189, 12 pgs.

Ross et al., "Anticipatory saccades during smooth pursuit eye movements and familial transmission of schizophrenia." Biological Psychiatry 44.8 (1998): 690-697.

Semmlow, John L., Gabriel M. GauthieR, and Jean-Louis Vercher. "Short term adaptive modification of saccadic amplitude." Eye Movements from Physiology to Cognition. Elsevier, 1987. 191-200. (Year: 1987).

\* cited by examiner

VESTIBULAR-OCULAR REFLEX TEST AND TRAINING SYSTEM

RELATED APPLICATIONS

This application claims priority to U.S. Provisional Patent Application 62/330,757, filed May 2, 2016, which is hereby incorporated by reference in its entirety. This application is also a continuation-in-part of U.S. patent application Ser. No. 14/454,662, filed Aug. 7, 2014, "System and Method for Cognition and Oculomotor Impairment Diagnosis Using Binocular Coordination Analysis," which claims priority to U.S. Provisional Patent Application No. 61/865,546, filed Aug. 13, 2013, all of which are hereby incorporated by reference in their entireties.

This application also related to U.S. patent application Ser. No. 10/834,356, filed Apr. 27, 2004, now U.S. Pat. No. 7,384,399, and U.S. patent application Ser. No. 13/506,840, filed May 18, 2012, now U.S. Pat. No. 9,004,687, both of which are hereby incorporated by reference in their entireties.

TECHNICAL FIELD

The disclosed embodiments relate generally to systems and methods of testing a subject's vestibular and ocular responses to a visual target, such as a stationary visual target, while the subject's head is in motion or the subject's head is stationary; cognitive and oculomotor impairment diagnosis using statistical analysis of error in the subject's ability to accurately focus on the visual target; and training the subject to improve their performance, and remediate or reduce cognitive and oculomotor impairment.

BACKGROUND

Pairing an action with anticipation of a sensory event is a form of attention that is crucial for an organism's interaction with the external world. The accurate pairing of sensation and action is dependent on timing and is called sensory-motor timing, one aspect of which is anticipatory timing. Anticipatory timing is essential to successful everyday living, not only for actions but also for thinking. Thinking or cognition can be viewed as an abstract motor function and therefore also needs accurate sensory-cognitive timing. Sensory-motor timing is the timing related to the sensory and motor coordination of an organism when interacting with the external world. Anticipatory timing is usually a component of sensory-motor timing and is literally the ability to predict sensory information before the initiating stimulus.

Anticipatory timing is essential for reducing reaction times and improving both movement and thought performance. Anticipatory timing only applies to predictable sensory-motor or sensory-thought timed coupling. The sensory modality (i.e., visual, auditory etc.), the location, and the time interval between stimuli, must all be predictable (i.e., constant, or consistent with a predictable pattern) to enable anticipatory movement or thought.

Without reasonably accurate anticipatory timing, a person cannot catch a ball, know when to step out of the way of a moving object (e.g., negotiate a swinging door), get on an escalator, comprehend speech, concentrate on mental tasks or handle any of a large number of everyday tasks and challenges. This capacity for anticipatory timing can become impaired with sleep deprivation, aging, alcohol, drugs, hypoxia, infection, clinical neurological conditions including but not limited to Attention Deficit Hyperactivity Disorder (ADHD), schizophrenia, autism and brain trauma (e.g., a concussion). For example, brain trauma may significantly impact a person's cognition timing, one aspect of which is anticipatory timing. Sometimes, a person may appear to physically recover quickly from brain trauma, but have significant problems with concentration and/or memory, as well as having headaches, being irritable, and/or having other symptoms as a result of impaired anticipatory timing. In addition, impaired anticipatory timing may cause the person to suffer further injuries by not having the timing capabilities to avoid accidents.

A fundamental vestibular function is control of eye motion during head motion, to maintain stable vision. Vestibular-ocular reflex function is the automatic compensation of the position of a person's visual focus for head movements. If a person's vestibular-ocular reflex is not functionally normally, a stationary target will appear to move when the person's head moves. Abnormal or substandard vestibular-ocular reflex function can result from traumatic brain injury (TBI), ingestion or exposure to drugs or alcohol, disease, or congenital or developmental deficit. As described in more detail below, the inventors have found that statistical analysis of errors in the position of a subject's visual focus, during head movement, and in some cases even while the person's head is not moving, can produce metrics that correspond to the quality of the subject's cognitive function and/or oculomotor impairment.

SUMMARY

Accordingly, there is a need to test a subject's vestibular-ocular reflex function, and in some embodiments the subject's anticipatory timing as well, in order to product metrics indicative of the quality of the subject's cognitive function and/or metrics indicative oculomotor impairment diagnosis. In some embodiments, one or more metrics, corresponding to quality of the subject's cognitive function and/or oculomotor impairment, are produced that correspond to a standard deviation, or variability, of error in the subject's eye position, relative to the position of a displayed object, during performance of a vestibular-ocular reflex function test. In some embodiments, one or more such metrics are generated using binocular coordination analysis.

Some implementations provide a method for cognition and oculomotor impairment diagnosis using vestibular-ocular reflex analysis. The method includes having the subject move their head in a specified manner (e.g., while moving the subject head left and right, or up and down, typically at repetition rate of between 0.2 and 2 Hz) while presenting the subject with a display of either a stationary or moving object (sometimes herein called a visual object) repeatedly moving over a tracking path (i.e., a visual object whose position is predictable by subjects with normal cognitive function), and, while presenting the display to the subject, measuring the subject's right eye positions and/or left eye positions. The test is typically performed over a period of 15 to 60 seconds, and is repeated two to ten time (e.g., three to six) times. Optionally, the method further includes measuring the subject's right eye positions and/or left eye positions while the subject's head is stationary, typically for a period of 10 to 30 seconds.

The method further includes generating one or more metrics, using statistical of the subject's right eye positions and/or left eye positions. In some embodiments, a respective metric of the one or more metrics corresponds to the variability of eye position error, where eye position error corresponds to the difference between the subject's actual eye position (e.g., for either the left or right eye) and the eye position corresponding to the actual position of a visual target, as displayed on a display.

In some embodiments, in addition to the vestibular-ocular reflex analysis, the method includes analysis of a person's dynamic visual acuity, conducted while an object that the person is trying to visually track is moved in synchronization with movement of the person's head. Optionally, analysis of the person's vestibular-ocular reflex function can be supplemented with analysis of the person's dynamic visual acuity.

In some embodiments, the one or more metrics include a disconjugacy metric generated by comparing the measured right eye positions with the measured left eye positions. In some embodiments, the method includes comparing the disconjugacy metric with a predetermined baseline to determine whether the disconjugacy metric is indicative of an impairment, and generating a report based on the disconjugacy metric.

In some implementations, the disconjugacy metric corresponds to a standard deviation of differences between the subject's right eye position and the subject's left eye position over a period of time during which the subject performs a respective test.

In some implementations, the predetermined baseline is based on at least one of: a disconjugacy range associated with a preselected group of control subjects, wherein the preselected group of control subjects have normal conjugate gaze; and a disconjugacy metric for the subject generated from a previous test.

In some embodiments, the method further comprises providing a distractor while measuring the subject's right eye and/or left eye positions ability; and generating a metric of distractibility, where the metric of distractibility is indicative of the subject's susceptibility to distraction. The generated report is based, at least in part, on the metric of distractibility. In some implementations, the distractor is the presentation of distracting visual stimuli adjacent or nearby the visual object being tracked by the subject, the presentation of unpredictable sounds, or audio task loading in which the subject is required to recite specific words or information while performing any of the tests described herein.

In some embodiments, the metric of distractibility is based on the difference between, a comparison of, or other combination of, a disconjugacy metric for a test performed without the provision of a distractor and a disconjugacy metric (herein sometimes called a stressed disconjugacy metric) for the same test performed with the provision of a distractor. In some implementations, the method includes comparing the stressed disconjugacy metric with the disconjugacy metric to determine whether the subject has a stress-sensitive impairment.

In some embodiments, the method includes generating one more metrics indicative of a cognitive impairment or oculomotor impairment.

In some embodiments, measuring the subject's eye positions is accomplished using one or more video cameras.

In accordance with some embodiments, a system includes one or more processors, memory, a display for displaying a visual object, eye position measurement apparatus for measuring eye position of a subject's right eye and/or left eye, and one or more programs stored in the memory. The one or more programs comprising instructions to present the subject with a display of a visual object, which is either stationary or repeatedly moving over a tracking path and, while presenting the display to the subject, measure the subject's right eye positions and/or the subject's left eye positions. The one or more programs further comprise instructions to generate one or more metrics corresponding to the subject's vestibular-ocular reflex function, based on the measurements of the subject's right eye positions and/or the subject's left eye positions.

In some embodiments, the one or more metrics include a disconjugacy metric generated by comparing the measured right eye positions with the measured left eye positions. In some embodiments, the disconjugacy metric is compared with a predetermined baseline to determine whether the disconjugacy metric is indicative of an impairment; and generate a report based on the disconjugacy metric.

In some implementations, the system further comprises a display on which the visual object is displayed and a measurement apparatus to measure the subject's right eye positions and/or left eye positions.

In some embodiments, the system includes head position tracking apparatus, for tracking position or movement of the subject's head.

In accordance with some implementations, an electronic device is provided that comprises one or more processors and memory storing one or more programs for execution by the one or more processors, the one or more programs including instructions for performing any of the methods described herein.

In accordance with some implementations, a computer-readable storage medium (e.g., a non-transitory computer readable storage medium) is provided, the computer-readable storage medium storing one or more programs for execution by one or more processors of an electronic device, the one or more programs including instructions for performing any of the methods described herein.

BRIEF DESCRIPTION OF THE DRAWINGS

Like reference numerals refer to corresponding parts throughout the several views of the drawings.

DETAILED DESCRIPTION OF EMBODIMENTS

It is very difficult to measure thinking performance without a movement. However, since a similar neural network is used for anticipatory timing, cognition and motor timing are linked. Therefore, diagnosis and therapy can be performed for anticipatory timing difficulties in the motor and cognitive domains using motor reaction times and accuracy. In particular, both the reaction time and accuracy of a subject's movements can be measured. As discussed below, these measurements can be used for both diagnosis and therapy.

Anticipatory cognition and movement timing are controlled by essentially the same brain circuits. Variability or a deficit in anticipatory timing produces imprecise movements and disrupted thinking, such as difficulty in concentration, memory recall, and carrying out both basic and complex cognitive tasks. Such variability and/or deficits leads to longer periods of time to successfully complete tasks and also leads to more inaccuracy in the performance of such tasks. Accordingly, in some embodiments, such variability is measured to determine whether a person suffers impaired anticipatory timing. In some embodiments, a sequence of stimuli is used in combination with a feedback mechanism to train a person to improve anticipatory timing.

Sequenced stimuli presented to a subject may include sequences of both predictable and non-predictable (e.g., random or pseudo-random) stimuli. In one embodiment, the non-predictable stimuli are presented to a subject before the predictable stimuli. The stimuli can use any sensory modality. In some embodiments, the stimuli are visual stimuli. In other embodiments, the stimuli are auditory. While other forms of stimuli can be used, the embodiments described here use visual stimuli. The subject's responses may be visual, manual or even spoken. In some embodiments, the subject's responses are measured by a mechanical, piezoelectric or other sensors activated by physical movement of the subject, such as pressing a button. In yet other embodiments, a frontal brain electroencephalographic (EEG) signal (e.g., the "contingent negative variation" signal) is measured during the period before a subject's response. The amplitude of the EEG signal is proportional to the degree of anticipation and will be disrupted when there are anticipatory timing deficits. In the embodiments described below, the subject's responses are measured by tracking eye movement.

Figure 1:
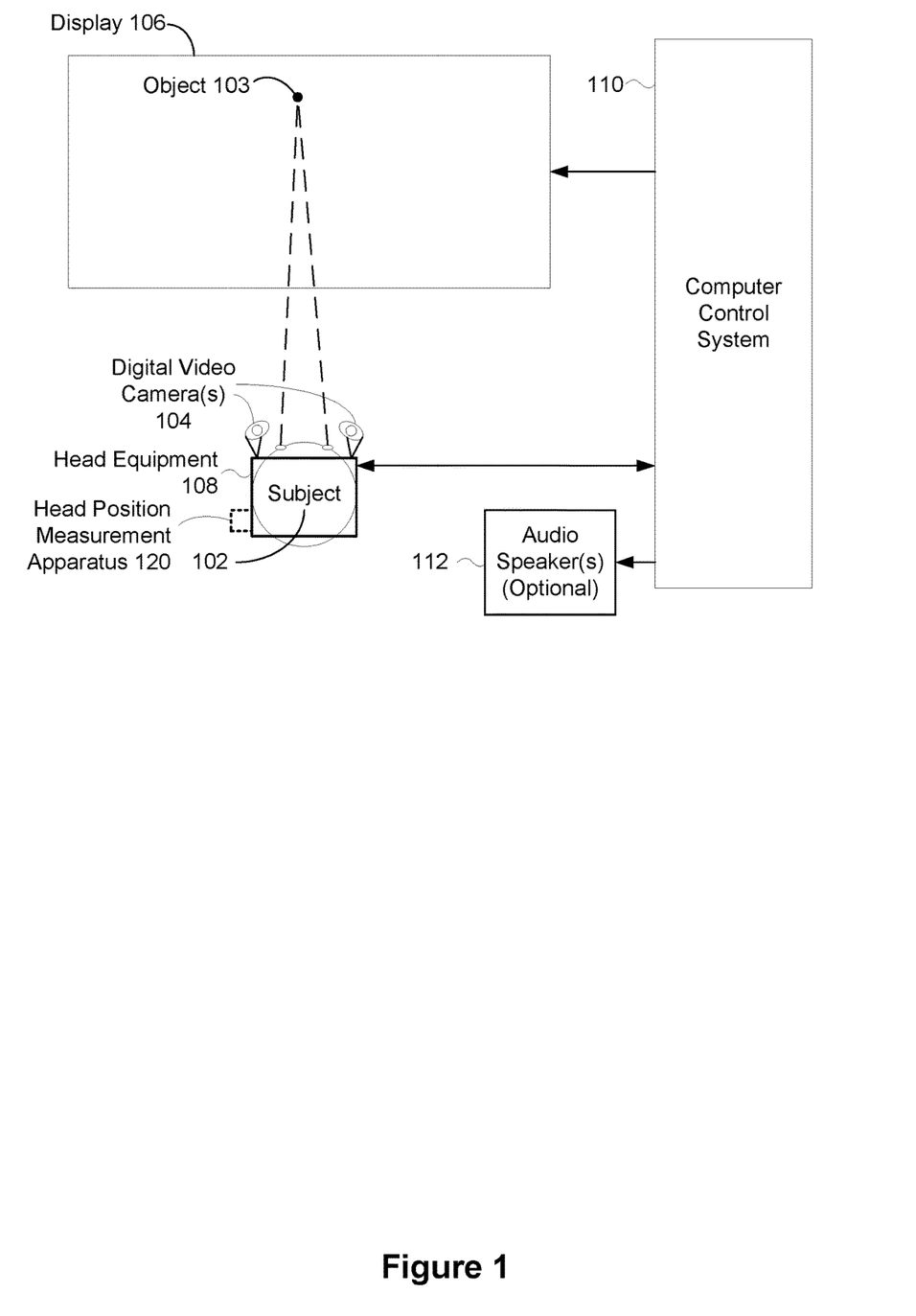
FIG. 1 is a block diagram illustrating a system for measuring a subject's ability to visually track a stationary or moving object while the subject's head moves horizontally or vertically within a predefined range of movement rates, in accordance with some embodiments.

FIG. 1 illustrates a system 100 for measuring a subject's ability to visually track a stationary or moving object in accordance with some embodiments. Subject 102 is shown a stationary or moving visual object 103 on display 106 (e.g., a screen). System 100 includes eye position measurement apparatus 104, typically including digital video cameras focused on subject 102'eyes so that eye positions (and, in some embodiments, eye movements) of subject 102 are recorded. In accordance with some embodiments, the eye position measurement apparatus 104 (e.g., the aforementioned digital video cameras) are mounted on subject 102'head by head equipment 108 (e.g., head equipment 108 includes a headband). Various mechanisms are, optionally, used to stabilize subject 102'head, for instance to keep the distance between subject 102 and display 106 fixed. In one embodiment, the distance between subject 102 and display 106 is kept fixed at approximately 40 cm. In some implementations, head equipment 108 includes the head equipment, or features of the head equipment, described in U.S. Pat. No. 9,004,687, which is incorporated by reference in its entirety.

Display 106 is, optionally, a computer monitor, projector screen, or other display device. Display 106 and eye position measurement apparatus 104 are coupled to computer control system 110. In some embodiments, computer control system 110 controls the visual object(s) displayed and also receives and analyses the eye position information received from eye position measurement apparatus 104 (e.g., digital video cameras). In some embodiments, computer control system 110 receives and analyses information about the subject's head position received from head position measurement apparatus 120, which measures either the position (e.g., the horizontal and/or vertical orientation of the subject's head) of the subject's head, and/or movement of the subject's head (e.g., horizontal and/or vertical movement of the subject's head). In some embodiments, head equipment 108 includes display 106, eye position measurement apparatus 104 (e.g., digital video cameras), and head position measurement apparatus 120 (e.g., a gyroscope, accelerometer, and/or other apparatus for detecting changes in orientation and/or changes in position of head equipment 108). In some embodiments, head equipment 108 is implemented, at least in part, in accordance with U.S. Pat. No. 9,004,687, which is hereby incorporated by reference. For example, head equipment 108 may be implemented by adding head position measurement apparatus 120 to the headset of U.S. Pat. No. 9,004,687.

In some embodiments, head equipment 108 includes eye position measurement apparatus 104 (e.g., digital video cameras), and head position measurement apparatus 120, but does not include a display and instead allows the subject to view an object outside head equipment while head equipment 108 determines the position of the subject's head, movement of the subject's head, and/or eye position of one or both eyes of the subject. In such embodiments, the object being viewed may be displayed on a display 106, as shown in FIG. 1, or may be a physical object positioned in front of or other known position relative to the subject.

In some embodiments, head equipment 108 includes virtual reality googles having embedded eye position measurement apparatus and head position measurement apparatus 120. In some embodiments of head equipment 108, the head equipment's embedded eye position measurement apparatus includes one or more infrared light sources to illuminate with infrared light one or more reference locations on the subject's eye or eyes and one or more video cameras, such as infrared video cameras, to detect the subject's pupil and the reference locations illuminated with infrared light.

Figure 2:
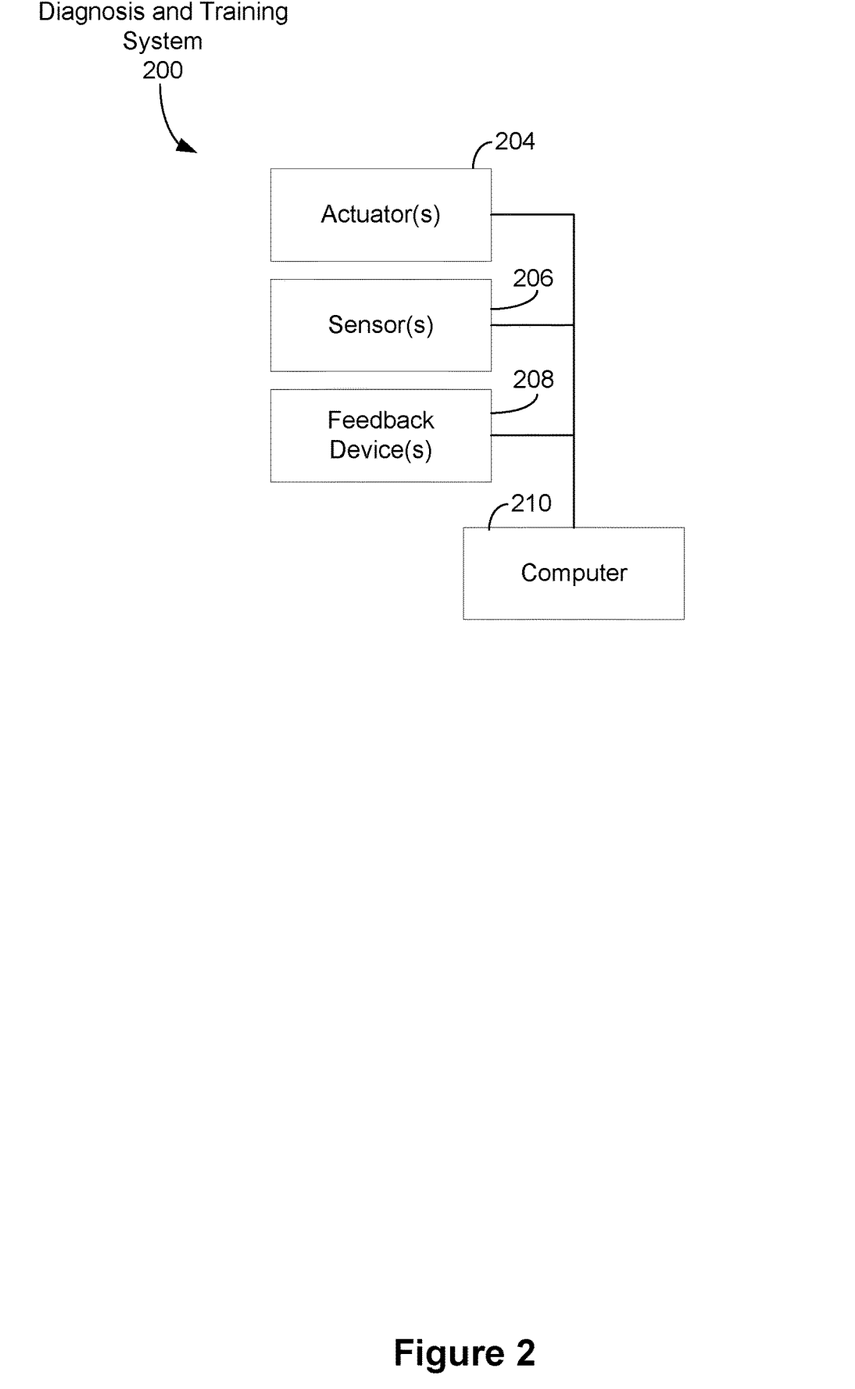
FIG. 2 is a conceptual block diagram illustrating a cognition timing diagnosis and training system in accordance with some embodiments.

FIG. 2 illustrates a conceptual block diagram of a diagnosis and training system 200, such as a cognitive function or vestibular-ocular reflex diagnosis and training system, in accordance with some embodiments. Diagnosis and training system 200 includes computer 210 (e.g., computer control system 110) coupled to one or more actuators 204, and one or more sensors 206. In some embodiments, system 200 includes one or more feedback devices 208 (e.g., when system 200 is configured for use as a cognitive timing training system). In some embodiments, feedback is provided to the subject via the actuators 204. In some embodiments, actuators 204 include a display device (e.g., display 106, FIG. 1) for presenting visual stimuli to a subject, audio speakers (e.g., audio speakers 112, FIG. 1) for presenting audio stimuli, a combination of the aforementioned, or one or more other devices for producing or presenting sequences of stimuli to a subject. In some embodiments, sensors 206 include visual sensors (e.g., a digital video camera(s) 104), optionally include head position measurement apparatus 120, and optionally include other types of sensors (e.g., a frontal brain electroencephalograph, and known as an EEG). Sensors 206 detect responses by a subject (e.g., subject 102 in FIG. 1) to sequences of stimuli presented by actuators 204, and optionally detection the position and/or movement of the subject's head during testing and/or training. Some types of sensors produce large amounts of raw data, only a small portion of which can be considered to be indicative of the user response. In such systems, computer 210 contains appropriate filters and/or software procedures for analyzing the raw data so as to extract "sensor signals" indicative of the subject's response to the stimuli and/or "sensor signals" indicative of the subject's head position or movement of the subject's head. In embodiments in which sensors 206 includes an electroencephalograph (EEG), the relevant sensor signal from the EEG may be a particular component of the signals produced by the EEG, such as the contingent negative variation (CNV) signal or the readiness potential signal.

Feedback devices 208 are, optionally, any device appropriate for providing feedback to the subject (e.g., subject 102 in FIG. 1). In some embodiments, feedback devices 208 provide real time performance information to the subject corresponding to measurement results, such as measurements results corresponding to the subject's vestibular-ocular reflex function, which enables the subject to try to improve his/her vestibular-ocular reflex function and cognitive function. In some embodiments, the performance information provides positive feedback to the subject when the subject's visual tracking (e.g., during vestibular-ocular reflex testing, and optionally other testing such as dynamic visual acuity testing) are within a normal range of values. In some embodiments, the one or more feedback devices 208 may activate the one or more actuators 204 in response to positive performance from the subject, such as by changing the color of the visual stimuli or changing the pitch or other characteristics of the audio stimuli.

Figure 3:
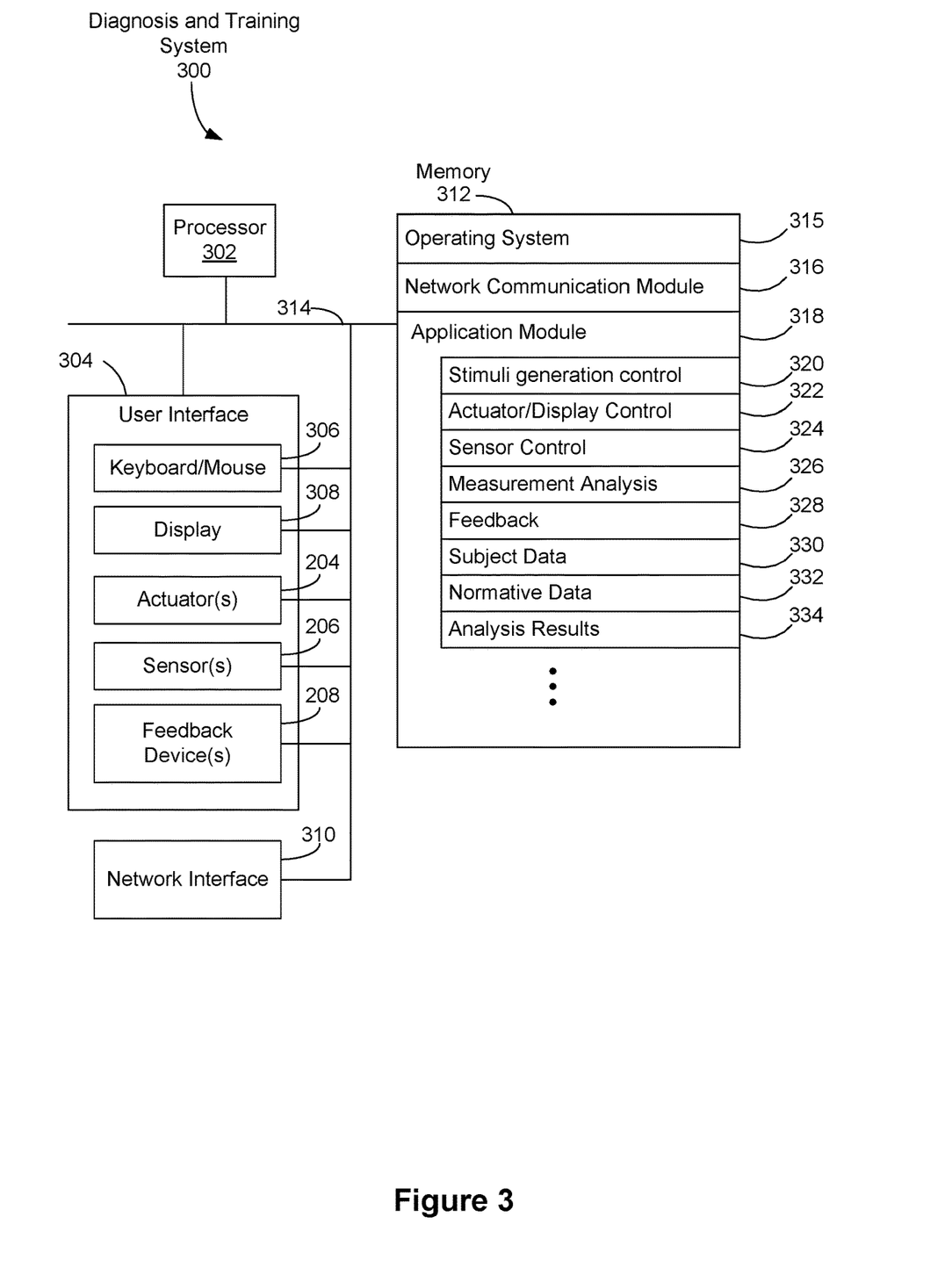
FIG. 3 is a detailed block diagram illustrating a cognition timing diagnosis and training system in accordance with some embodiments.
Figure 4A:
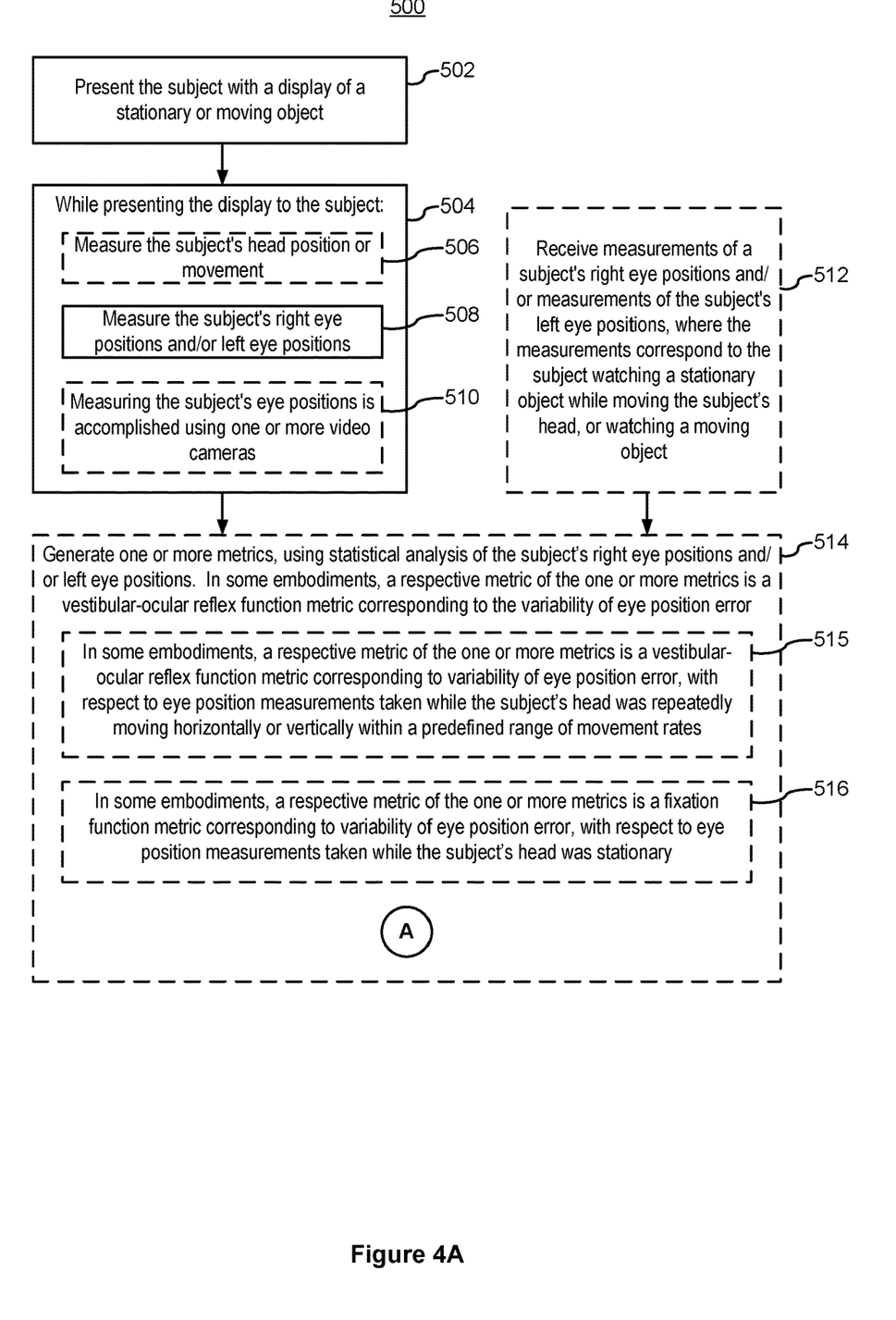
FIGS. 4A-4C are flow diagrams illustrating a method for vestibular-ocular reflex function testing and impairment diagnosis in accordance with some embodiments.
Figure 4B:
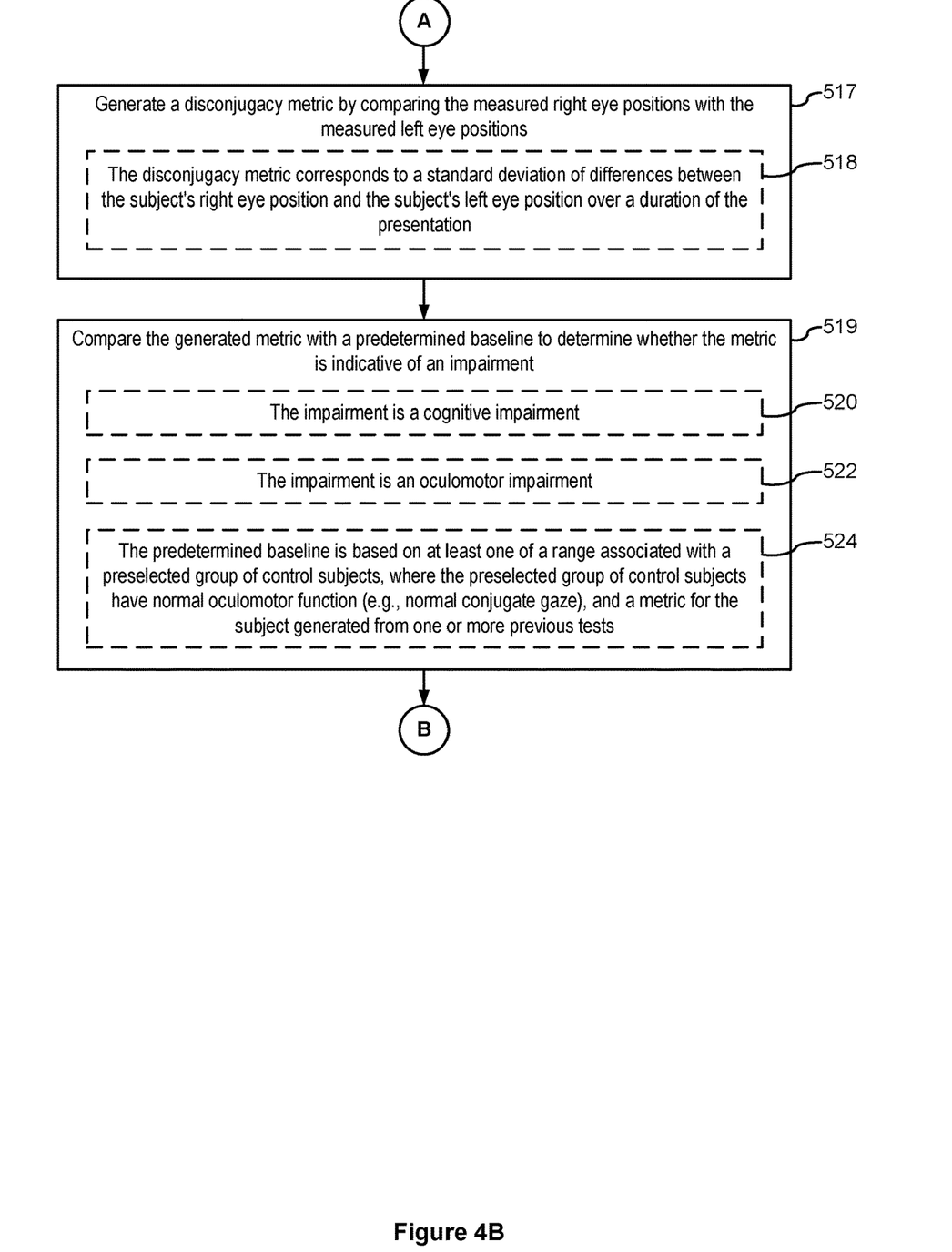
Figure 4C:
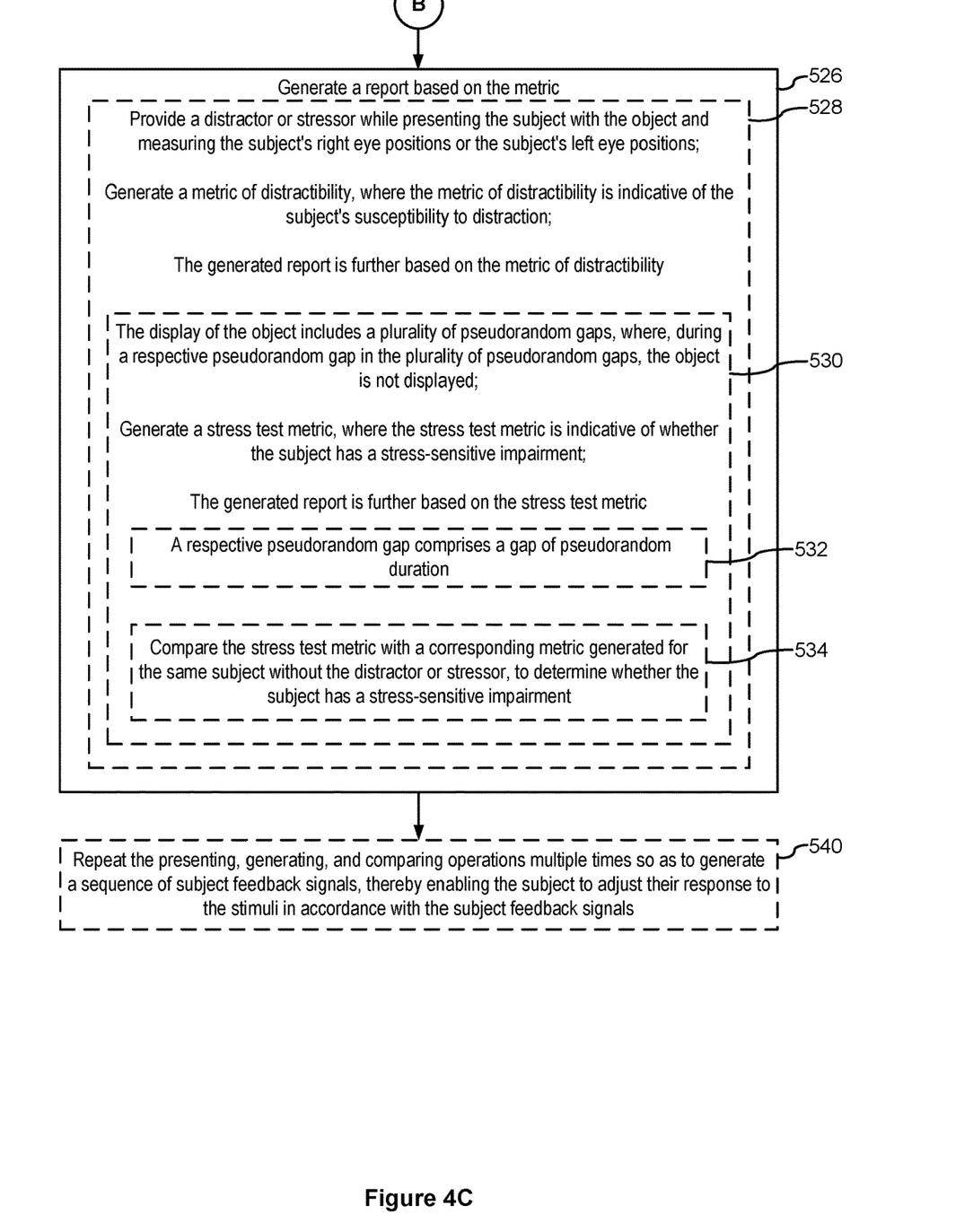

FIG. 3 is a block diagram of a diagnosis and training system 300, such as a cognitive function or vestibular-ocular reflex diagnosis and training (or remediation) system, in accordance with some embodiments. The system 300 includes one or more processors 302 (e.g., CPUs), user interface 304, memory 312, and one or more communication buses 314 for interconnecting these components. In some embodiments, the system includes one or more network or other communications interfaces 310, such as a network interface for conveying testing or training results to another system or device. The user interface 304 includes at least one or more actuators 204 and one or more sensors 206, and, in some embodiments, also includes one or more feedback devices 208. In some embodiments, the user interface 304 further includes additional computer interface devices such as keyboard/mouse 306 and display 308. In some embodiments, the display is coupled with one of actuators 204.

In some implementations, memory 312 includes a non-transitory computer readable medium, such as high-speed random access memory and/or non-volatile memory (e.g., one or more magnetic disk storage devices, one or more flash memory devices, one or more optical storage devices, and/or other non-volatile solid-state memory devices). In some implementations, memory 312 includes mass storage that is remotely located from processing unit(s) 302. In some embodiments, memory 312 stores an operating system 315 (e.g., Microsoft Windows, Linux or Unix), an application module 318, and network communication module 316.

In some embodiments, application module 318 includes stimuli generation control module 320, actuator/display control module 322, sensor control module 324, measurement analysis module 326, and, optionally, feedback module 328. Stimuli generation control module 320 generates sequences of stimuli, as described elsewhere in this document. Actuator/display control module 322 produces or presents the sequences of stimuli to a subject. Sensor control module 324 receives sensor signals and, where appropriate, analyzes raw data in the sensor signals so as to extract sensor signals indicative of the subject's (e.g., subject 102 in FIG. 1) response to the stimuli. In some embodiments, sensor control module 324 includes instructions for controlling operation of sensors 206. Measurement analysis module 326 analyzes the sensor signals to produce measurements and analyses, as discussed elsewhere in this document. Feedback module 328, if included, generates feedback signals for presentation to the subject via the display 208, one or more actuators 204 or feedback devices 208.

In some embodiments, during any of the tests described herein (e.g., vestibular-ocular reflex function testing), and/or during remedial training, feedback is presented to the subject in accordance with a metric (e.g., a metric generated by statistical analysis of the measurements of subject's right eye positions or the subject's left eye positions) while continuing to present an object (e.g., object 103, FIG. 1) to the subject and while the subject's head continues to move horizontally or vertically within a predefined range of movement rates, so as to train the subject to improve the subject's cognitive or oculomotor performance. In some embodiments, presenting feedback to the subject includes varying an aspect of the feedback in accordance with a difference between the metric and a target value or baseline value of the metric.

In some embodiments, presenting feedback to the subject includes presenting a feedback object and varying a size or color of the feedback object in accordance with a difference between the metric and a target value or baseline value of the metric. For example, during vestibular-ocular reflex function testing, and/or during remedial training, feedback is presented to the subject by displaying a circle or other feedback object (e.g., using display 308 or feedback device 208, FIG. 3) surrounding or nearby the object being visually tracked by the subject, and the color and/or size of the feedback object are dynamically changed to indicate the quality of the subject's performance. In a more specific example, the size of the feedback object may decrease when the subject's performance improves, shrinking to a predefined size when the subject's performance meets predefined criteria, and may increase when the subject's performance worsens. In some embodiments, system 300 varies the size of the feedback object based on (e.g., a predefined function of) the difference between a measurement metric (e.g., the variability or standard deviation of eye position error, such as horizontal eye position error or vertical eye position error, depending on the direction or movement of the subject's head during the vestibular-ocular reflex function testing) and a target value or baseline value of the metric. Alternatively, or in addition, system 300 varies the color of the feedback object, or the color of the object being tracked, or the color of a displayed background that forms a background for the object being tracked, based on (e.g., a predefined function of) the difference between a measurement metric (e.g., the variability or standard deviation of eye position error, such as horizontal eye position error or vertical eye position error, depending on the direction or movement of the subject's head during the vestibular-ocular reflex function testing) and a target value or baseline value of the metric.

In some embodiments, application module 318 furthermore stores subject data 330, which includes the measurement data for a subject, and analysis results 334 and the like. In some embodiments, application module 318 stores normative data 332, which includes measurement data from one or more control groups of subjects, and optionally includes analysis results 334, and the like, based on the measurement data from the one or more control groups. In some embodiments, subject data 330 includes data of a subject's changing performance over time, such as changes in performance during remedial training.

Still referring to FIG. 3, in some embodiments, sensors 206 include one or more digital video cameras focused on the subject's pupil (e.g., digital video cameras 104), operating at a picture update rate 30 hertz or more. In some embodiments, the picture update rate is 100 hertz to 500 hertz. In some embodiments, the one or more digital video cameras are infrared cameras, while in other embodiments, the cameras operate in other portions of the electromagnetic spectrum. In some embodiments, the resulting video signal is analyzed by processor 302, under the control of measurement analysis module 326, to determine the screen position(s), sometimes herein called gaze positions, where the subject focused, and the timing of when the subject focused at one or more predefined screen positions. For purposes of this discussion, the location of a subject's focus is the center of the subject's visual field. For example, using a picture update rate of 100 hertz, during a predefined test period of N seconds (e.g., 30 seconds), N×100 gaze position measurements are obtained, or 3000 gaze position measurements in 30 seconds. In another example, using a picture update rate of 500 hertz, during a predefined test period of N seconds (e.g., 30 seconds), N×500 gaze position measurements are obtained, or 15,000 gaze position measurements in 30 seconds.

In some embodiments, not shown, the system shown in FIG. 3 is divided into two systems, one which tests a subject and collects data, and another which receives the collected data, analyzes the data and generates one or more corresponding reports.

For purposes of this discussion the terms "normal subject" and "abnormal subject" are defined as follows. Normal subjects are healthy individuals without any known or reported impairments to brain function. Abnormal subjects are individuals suffering from impaired brain function with respect to sensory-motor or anticipatory timing.

In some embodiments, the width of a subject's anticipatory timing distribution is defined as the variance of the response distribution, the standard deviation of the response distribution, the average deviation of the response distribution, the coefficient of variation of the response distribution, or any other appropriate measurement, sometimes called a statistical measurement, of the width of the response distribution.

The subject's anticipatory timing distribution can be compared with the anticipatory timing distribution of a control group of subjects. Both the average timing and the width of the timing distribution, as well as their comparison with the same parameters for a control group are indicative of whether the subject is suffering from a cognitive timing impairment.

Calibration. In some embodiments, in order to provide accurate and meaningful real time measurements of where the user's is looking at any one point in time, the eye position measurements (e.g., produced via digital video cameras 104) are calibrated by having the subject focus on a number of points on a display (e.g., display 106) during a calibration phase or process. For instance, in some embodiments, calibration may be based on nine points displayed on the display, include a center point, positioned at the center of the display locations to be used during testing of the subject, and eight points along the periphery of the display region to be used during testing of the subject. The subject is asked to focus on each of the calibration points, in sequence, while digital video cameras (e.g., digital video cameras 104) measure the pupil and/or eye position of the subject. The resulting measurements are then used by a computer control system (e.g., computer control system 110) to produce a mapping of eye position to screen location, so that the system can determine the position of the display at which the user is looking at any point in time. In other embodiments, the number of points used for calibration may be more or less than nine points, and the positions of the calibration points may be distributed on the display in various ways.

In some implementations, the calibration process is performed each time a subject is to be tested, because small differences in head position relative to the cameras, and small differences in position relative to the display 106, can have a large impact on the measurements of eye position, which in turn can have a large impact of the "measurement" or determination of the display position at which the subject is looking. The calibration process can also be used to verify that the subject (e.g., subject 102) has a sufficient range of oculomotor movement to perform the test.

Oculomotor Testing. In some embodiments, after calibration is completed, the subject is told to look at an object (e.g., a dot or ball) on the display and to do his/her best to maintain the object at the center of his/her vision as it moves, or as it remains stationary while the subject moves his or her head in a repeating pattern (e.g., horizontal movement, left and right, or vertical movement, up and down, at a rate of 0.1 to 1.0 hertz) while keeping the object in view.

In some embodiments, stimuli generation control module 320 generates or controls generation of the visual object and determination of its tracking path, if any, and actuator/display control module 322 produces or presents the sequences of stimuli to the subject.

In some embodiments, the subject is asked to focus on an object that is not moving, for a predefined test period of T seconds (e.g., 15 seconds, or any suitable test period having a duration of 10 to 60 seconds), measurements are made of how well the subject is able to maintain focus (e.g., the center of the subject's visual field) on the object during the test period, and an analysis, similar to other analyses described herein, is performed on those measurements. In some circumstances, this "non-moving object" test is performed on the subject in addition to other test(s) described herein, and results from the analyses of measurements taken during both the non-moving object test and other tests are used to evaluate the subjects cognitive function. In some embodiments, the non-moving object test is performed while the subject moves his or her head in a repeating pattern (e.g., horizontal movement, left and right, or vertical movement, up and down, at a rate of 0.1 to 1.0 hertz) while keeping the object in view, in which case the test is optionally called a vestibular-ocular reflex function test.

In accordance with some implementations, the pictures taken by the cameras are converted into display locations (hereinafter called subject eye positions), indicating where the subject was looking at each instant in time recorded by the cameras. In some embodiments, the subject eye positions are compared with the actual displayed object positions. In some embodiments, the data representing eye and object movements is low-pass filtered (e.g., at 50 Hz) to reduce signal noise. In some embodiments, saccades, which are fast eye movements during which the subject catches up with the moving displayed object, are detected and counted. In some embodiments, eye position measurements during saccades are replaced with extrapolated values, computed from eye positions preceding each saccade. In some other embodiments, eye position and velocity data for periods in which saccades are detected are removed from the analysis of the eye position and velocity data. The resulting data is then analyzed to generate one or more of the derived measurements or statistics discussed below.

In some embodiments, the measurements described above are taken while the subject is presented with a stationary object, and the subject's head moves horizontally or vertically within a predefined range of movement rates. Such testing is sometimes called vestibular-ocular reflex testing.

Disconjugacy of Binocular Coordination. Many people have one dominate eye (e.g., the right eye) and one subservient eye (e.g., the left eye). For these people, the subservient eye follows the dominate eye as the dominate eye tracks an object (e.g., object 103 in FIG. 1). In some embodiments, a disconjugacy metric is calculated to measure how much the subservient eye lags behind the dominate eye while the dominate eye is tracking an object. Impairment due to sleep deprivation, aging, alcohol, drugs, hypoxia, infection, clinical neurological conditions (e.g., ADHD, schizophrenia, and autism), and/or brain trauma (e.g., head injury or concussion) can increase the lag (e.g., in position or time) or differential (e.g., in position or time) between dominate eye movements and subservient eye movements, and/or increase the variability of the lag or differential, and thereby increase the corresponding disconjugacy metric.

In some embodiments, the disconjugacy of binocular coordination is the difference between the left eye position and the right eye position at a given time, and is calculated as:

$$\text{Disconj}(t) = POS_{LE}(t) - POS_{RE}(t)$$

where "t" is the time and "$POS_{LE}(t)$" is the position of the subject's left eye at time t and "$POS_{RE}(t)$" is the position of the subject's right eye at time t. In various embodiments, the disconjugacy measurements include one or more of: the difference between the left eye position and the right eye position in the vertical direction (e.g., $POS_{RE_x}(t)$ and $POS_{LE_x}(t)$); the difference between the left eye position and the right eye position in the horizontal direction (e.g., $POS_{RE_y}(t)$ and $POS_{LE_y}(t)$); the difference between the left eye position and the right eye position in the two-dimensional horizontal-vertical plane (e.g., $POS_{RE_{xy}}(t)$ and $POS_{LE_{xy}}(t)$); and a combination of the aforementioned.

In some embodiments, a test includes three identical trials of 12 orbits. To quantify the dynamic change of disconjugacy during a test, the data from each trial is aligned in time within each test and the standard deviation of disconjugate eye positions (SDDisconj) is calculated. In accordance with some embodiments, SDDisconj for a set of "N" values is calculated as:

$$SDDisconj_N = \sqrt{\frac{1}{N}\sum_{i=1}^{N}(x_i - \langle x \rangle)^2}$$

where "x" is a disconjugate measurement discussed above (e.g., Disconj(t)) and "⟨x⟩" represents the average value of the disconjugate eye positions. Thus, in various embodiments, $SDDisconj_N$ represents: the standard deviation of disconjugate eye positions in the vertical direction; the standard deviation of disconjugate eye positions in the horizontal direction; or the standard deviation of disconjugate eye positions in the two-dimensional horizontal-vertical plane. In some embodiments, a separate SDDisconj measurement is calculated for two or more of the vertical direction, the horizontal direction, and the two-dimensional horizontal-vertical plane.

Therefore, in various embodiments, disconjugacy measurements, standard deviation of disconjugacy measurements, tracking measurements, and related measurements (e.g., a variability of eye position error measurement, a variability of eye velocity gain measurement, an eye position error measurement, a rate or number of saccades measurement, and a visual feedback delay measurement) are calculated. Furthermore, in various embodiments, the disconjugacy measurements, standard deviation of disconjugacy measurements, tracking measurements, and related measurements are calculated for one or more of: the vertical direction; the horizontal direction; the two-dimensional horizontal-vertical plane; and a combination of the aforementioned.

In some embodiments, one or more of the above identified measurements are obtained for a subject and then compared with the derived measurements for other individuals. In some embodiments, one or more of the above identified measurements are obtained for a subject and then compared with the derived measurements for the same subject at an earlier time. For example, changes in one or more derived measurements for a particular person are used to evaluate improvements or deterioration in the person's ability to anticipate events. Distraction and fatigue are often responsible for deterioration in the person's ability to anticipate events, and more generally the person's oculomotor function and cognitive function. In some embodiments, decreased attention, caused by fatigue or a distractor, can be measured by comparing changes in one or more derived measurements for a particular person.

In some embodiments, measurements of the subject's eye position are taken while the subject is presented with a stationary object, and the subject's head moves horizontally or vertically within a predefined range of movement rates. As noted above, such testing is sometimes called vestibular-ocular reflex testing.

In some embodiments, the measurements described above are taken while the subject is presented with an object (e.g., an object displayed on a screen or computer display) that moves in a manner synchronized with and in a same direction as movements of the subject's head. In some such embodiments, the object is moved horizontally to the left when the subject's head moves to the left, and to the right when the subject's head moves to the right. Similarly, in some such embodiments, the object is moved vertically upward when the subject's head moves upward, and downward when the subject's head moves downward. Furthermore, in some such embodiments, the object is moved in synchronization with movements of the user's head by an amount that maintains a substantially constant angle between the displayed object and a direction determined by the subject's head position (e.g., a predefined forward gaze direction, normal to a plane defined by the subject's eyes and head tilt).

In some embodiments, analysis of the measurements and presentation of a report or feedback based on the analysis, described in more detail elsewhere in this document, is performed while measurements (e.g., eye position measurements and head position or movement measurements) are still being taken, during a current iteration of a test or training session.

Diagnostic Method. FIGS. 5A-5C are flow diagrams representing a method 500 for cognitive function and/or oculomotor function (e.g., vestibular-ocular reflex function) testing and diagnosis, in accordance with some embodiments. In some embodiments, method 500 includes remedial training, as described below. In some implementations, method 500 is performed at a system including one or more processors and memory storing instructions for execution by the one or more processors (e.g., system 200). For example, FIG. 1 shows a system in which subject 102 presented with display 106 including object 103. FIG. 1 further shows digital video cameras 104 for measuring subject 102'eye positions, and head position measurement apparatus 120 for measuring the position (e.g., horizontal and/or vertical angular position) of the subject's head and/or movement of the subject's head.

Method 500 is, optionally, governed by instructions stored in a computer memory or non-transitory computer readable storage medium (e.g., memory 312 in FIG. 3) and executed by one or more processors (e.g., processor 302) of one or more computer systems, including, but not limited to, the computer control system 110, and/or computer 210. The computer readable storage medium may include a magnetic or optical disk storage device, solid state storage devices such as Flash memory, or other non-volatile memory device or devices. The computer readable instructions stored on the computer readable storage medium may include one or more of: source code, assembly language code, object code, or other instruction format that is interpreted by one or more processors. In various implementations, some operations in each method may be combined and/or the order of some operations may be changed from the order shown in the figures. Also, in some implementations, operations shown in separate figures and/or discussed in association with separate methods may be combined to form other methods, and operations shown in the same figure and/or discussed in association with the same method may be separated into different methods. Moreover, in some implementations, one or more operations in the methods are performed by modules of cognitive diagnosis and training system 200 and/or the system 300 shown in FIG. 3, including, for example, operating system processor 302, user interface 304, memory 312, network interface 310, and/or any sub modules thereof.

The system presents (502) the subject a stationary object, or alternatively with a moving object (e.g., a displayed, moving object). The rate of movement, if any, of the object, the path over which the object moves, the periods of time over which the object is displayed, and the apparatus used to accomplish these functions are described above. For example, FIG. 1 shows subject 102 presented with an object 103 on display 106.

In some embodiments, the subject is instructed to repeatedly move his or her head horizontally back and forth, or vertically up and down, while keeping the visual object in view, at a rate of 0.1 to 1.0 hertz, and while the subject is moving his or head in this manner, and the visual object is being presenting on the display to the subject (504), the system measures (508) the subject's right eye positions and/or the subject's left eye positions. Optionally, while the subject is moving his or head in this manner, and the visual object is being presenting on the display to the subject (504), the system also measures (506) the position (e.g., horizontal and/or vertical angular position) of the subject's head and/or movement of the subject's head. The subject's head position or head movement is measured (506), in some embodiments, to ensure that the rate of head movement falls within a predefined range or movement rates, such as 0.1 to 1.0 hertz. In some embodiments, the system is configured (e.g., includes one or more programs with instructions) to verify that the subject's head moves horizontally or vertically within the predefined range of movement rates. In some such embodiments, the rate of movement of the subject's head must fall within the predefined range in order to generate valid metrics with respect to vestibular-ocular reflex function and/or cognitive function of the subject.

In some embodiments, the subject is asked to focus on an object that is not moving, for a predefined test period of T seconds (e.g., 15 seconds, or any suitable test period having a duration of 10 to 60 seconds), measurements are made of how well the subject is able to maintain focus (e.g., the center of the subject's visual field) on the object during the test period, and an analysis, similar to other analyses described herein, is performed on those measurements. In some circumstances, this "non-moving object" test is performed on the subject in addition to other tests described herein, and results from the analyses of measurements taken during both the non-moving object test and other tests are used to evaluate the subjects cognitive function. In some embodiments, the non-moving object test is performed while the subject's head is stationary, or while the subject moves his or her head in a repeating pattern (e.g., horizontal movement, left and right, or vertical movement, up and down, at a rate of 0.1 to 1.0 hertz) while keeping the object in view, in which case the test is optionally called a vestibular-ocular reflex function test.

In another variation, operations 502 and 504 of method 500 include measuring the subject's head position or movement, and the subject's right eye position and/or left eye position, while moving a displayed object in synchronization with movement of the subject's head. Additional details of such synchronized movement of the object and subject's head are described above. Optionally, analysis of such eye movements is called analysis of the subject's dynamic visual acuity.

In some embodiments, measuring the subject's eye positions is accomplished (510) by using one or more video cameras. In accordance with these embodiments, FIG. 1 shows a system 100 including digital video cameras 104 for measuring subject 102'eye positions.

In some embodiments, the system receives (512) measurements of the subject's right eye positions and/or measurements of the subject's left eye positions, where the measurements correspond to the subject watching a stationary object (e.g., watching a stationary object while repeatedly moving the subject's head back and forth or up and down) or watching a moving object, which moves in synchronization with movement of the subject's head. In some embodiments, the system receives the measurements from a remote system or device. In some embodiments, the system receives the measurements from a user.

Method 500 further includes generating (514) one or more metrics, using statistical analysis of the subject's right eye positions and/or left eye positions. In some embodiments, a respective metric of the one or more metrics is a vestibular-ocular reflex function metric (515) corresponding to the variability of eye position error, where eye position error corresponds to the difference between the subject's actual eye position (e.g., for either the left or right eye) and the eye position corresponding to the actual position of a visual target.

In some embodiments, a respective metric of the one or more generated metrics is a standard deviation of eye position error, of the subject's right eye or left eye, or is a function (e.g., a linear or non-linear function) of the standard deviation of eye position error, with respect to a eye position measurements taken over a contiguous period of time (e.g., typically having a duration of 10 to 120 seconds) during which the subject performs an individual test or individual remedial training exercise. In some embodiments, the metric is generated for a sequence of periods of time, e.g., with respect to a moving window of time, during which the subject performs an individual test or individual remedial training exercise, thereby allowing the subject to be presented with a sequence of feedback or reports, which change as the generated metric is updated, while the individual test or individual remedial training exercise is still being performed.

In some embodiments, the one or more metrics includes a respective vestibular-ocular reflex function metric that corresponds to eye position measurements taken while the subject's head was repeatedly moving horizontally or vertically within a predefined range of movement rates, and while the visual object (as displayed) was not moving.

In some embodiments, the one or more metrics includes a respective metric (516) that corresponds to eye position measurements taken while the subject's head was repeatedly moving horizontally or vertically within a predefined range of movement rates and the visual object (as displayed) was stationary, or alternatively was moving in a predefined repeating pattern, for example moving in accordance with any of the patterns described above.

In some embodiments, a respective metric of the one or more metrics is a fixation function metric corresponding to the variability of eye position error, where eye position error corresponds to the difference between the subject's actual eye position (e.g., for either the left or right eye) and the eye position corresponding to the actual position of a visual target. The fixation function metric furthermore corresponds to eye position measurements taken while the subject's head was stationary (e.g., moving less than a predefined amount during performance of the test). In some embodiments, the one or more metrics includes a fixation function metric that corresponds to eye position measurements taken while the subject's head was stationary (e.g., moving less than a predefined amount during performance of the test), and the visual object (as displayed) was stationary. In some embodiments, the one or more metrics includes a fixation function metric that corresponds to eye position measurements taken while the subject's head was stationary (e.g., moving less than a predefined amount during performance of the test) and the visual object (as displayed) was moving in a predefined repeating pattern, for example moving in any of the repeating patterns described above.

In some embodiments, the one or more metrics includes (517) a disconjugacy metric generated by comparing the measured right eye positions with the measured left eye positions. In some embodiments, as described in more detail above, generating the disconjugacy metric includes calculating a difference metric by subtracting the relative position of the subject's right eye from the relative position of the subject's left eye. In some embodiments, generating the disconjugacy metric includes averaging over each of a plurality of difference metrics, where each difference metric corresponds to a distinct time. In some embodiments, generating the disconjugacy metric includes generating a vertical metric and generating a horizontal metric, where generating a vertical metric includes measuring the difference between the subject's eyes along a vertical axis and generating a horizontal metric includes measuring the difference between the subject's eyes along a horizontal axis.

In some embodiments, the disconjugacy metric corresponds (518) to a standard deviation of differences between the subject's right eye position and the subject's left eye position over a contiguous period of time (e.g., typically having a duration of 10 to 120 seconds) during which the subject performs an individual test or individual remedial training exercise. In some embodiments, the disconjugacy metric is generated for a sequence of periods of time, e.g., with respect to a moving window of time, during which the subject performs an individual test or individual remedial training exercise, thereby allowing the subject to be presented with a sequence of feedback or reports, which change as the generated disconjugacy metric is updated, while the individual test or individual remedial training exercise is still being performed.

In some embodiments, the system compares (519) the generated metric (e.g., a vestibular-ocular reflex metric, the aforementioned disconjugacy metric, or any of the other metrics described herein) with a predetermined baseline to determine whether the metric is indicative of an impairment. In some embodiments, the impairment is (520) a cognitive impairment (e.g., an anticipatory timing impairment). For example, the impairment causes an inability to focus (e.g., ADHD). In some embodiments, the impairment detected by method 500 is (522) an oculomotor impairment.

In some embodiments, the predetermined baseline is (524) based on at least one of: a range associated with a preselected group of control subjects, where the preselected group of control subjects have normal oculomotor function (e.g., normal conjugate gaze), sometimes called a control group baseline; and a metric for the subject generated from one or more previous tests, sometimes called an individual or personal baseline. In some embodiments, the group of control subjects is composed of persons having a similar age and socioeconomic status as the subject. In some embodiments, the group of control subjects is composed of persons having a similar brain development level as the subject. In some embodiments, the group of control subjects is composed of persons of the same gender as the subject. In some embodiments or in some circumstances, an increase in the metric (e.g., a vestibular-ocular reflex metric, the aforementioned disconjugacy metric, or any of the other metrics described herein) between subsequent tests may be indicative of fatigue, impaired mental state induced by drugs/alcohol, or recent trauma.

The system generates (526) a report based on the one or more generated metrics (e.g., see description of operation 514 regarding generation of one or more metrics). In some embodiments, the system presents the report to the subject, test administrator or other user. In some embodiments, the report is stored in memory (e.g., stored in memory 312 as analysis results 334) for further analysis. In some embodiments, the report is used to generate a new baseline metric for future comparisons (e.g., the report is used to generate normative data 332 and/or subject data 330).

In some embodiments, the system provides (528) a distractor or stressor while presenting the subject with the object (e.g., object 103, FIG. 1) and measuring the subject's right eye positions or the subject's left eye positions (for example, during performance of any of the testing methods or remedial training methods described herein). In some implementations, the distractor is the presentation of distracting visual stimuli (e.g., bright flashes of light, flashing images, or moving or varying a background image) adjacent or nearby the visual object being tracked by the subject, or the presentation of unpredictable sounds, or audio task loading in which the subject is required to recite specific words or information (e.g., counting backwards) while performing any of the tests described herein. In some embodiments, the presentation of unpredictable sounds includes presenting sounds through headphones or speakers (e.g., audio speakers 112, FIG. 1) at times that are unpredictable from the perspective of the subject. Optionally, the unpredictable sounds are presented at auditory volumes loud enough to be distracting. Optionally, the unpredictable sounds include auditory bursts of varying duration (e.g., varying between 0.1 and 1.0 seconds in duration) that is unpredictable from the perspective of the subject.

The system generates a metric of distractibility, where the metric of distractibility is indicative of the subject's susceptibility to distraction. The generated report is further based on the metric of distractibility.

In some embodiments, providing a stressor (528) includes displaying the object with a plurality of pseudorandom gaps (530), where, during a respective pseudorandom gap in the plurality of pseudorandom gaps, the object is not displayed. The system generates a stress test metric, where the stress test metric is indicative of whether the subject has a stress-sensitive impairment (e.g., post-traumatic stress disorder (PTSD)). The generated report is further based on the stress test metric. In some embodiments, the display of the object includes 3 to 10 gaps, each having a duration of 0.1 to 1.0 seconds, during which the object is not displayed) over a period of 15 seconds to a minute. In some embodiments, the pseudorandom gaps occur at random times from the perspective of the subject. In some embodiments, the pseudorandom gaps are unknown in advance by the subject, but are on a preset schedule.

In some embodiments, a respective pseudorandom gap has (532) a pseudorandom duration. For example, in some embodiments, the pseudorandom duration is selected from one of three potential durations (e.g., 0.1, 0.3 and 0.5 seconds).

In some embodiments, the system compares (534) the stress test metric with a corresponding metric (sometimes variously called the corresponding non-stress metric, or standard metric) generated for the same subject without the distractor or stressor, to determine whether the subject has a stress-sensitive impairment (e.g., PTSD). For example, in accordance with some implementations, if the stress test metric is significantly higher than the corresponding non-stress metric (e.g., if the stress test metric exceeds the corresponding non-stress metric by more than a predefined threshold) then it indicates that the subject suffers from a stress-sensitive impairment (e.g., PTSD).

In some embodiments, the system repeats (540) the presenting (502), measuring (504), generating (514), and comparing (e.g., 519) operations multiple times so as to generate a sequence of subject feedback signals, thereby enabling the subject to adjust their response to the stimuli in accordance with the subject feedback signals. For example, the sequence of steps 502-538, or a subset thereof, are repeatedly performed so as to help train a subject to improve his/her cognitive performance (e.g., by improving anticipatory timing) and/or oculomotor performance, and thereby remediate or reduce cognitive and/or oculomotor impairment.

In some embodiments, during performance of any of the aforementioned cognitive or oculomotor tests, and/or during remedial training (e.g., during operation 540), feedback is presented to the subject in accordance with a metric (e.g., a metric generated by statistical analysis of the measurements of subject's right eye positions or the subject's left eye positions) while continuing to present an object (e.g., object 103, FIG. 1) to the subject and while the subject's head continues to move horizontally or vertically within a predefined range of movement rates, so as to train the subject to improve the subject's cognitive or oculomotor performance. In some embodiments, presenting feedback to the subject includes varying an aspect of the feedback in accordance with a difference between the metric and a target value or baseline value of the metric.

In some embodiments, presenting feedback to the subject includes presenting a feedback object and varying a size or color of the feedback object in accordance with a difference between the metric and a target value or baseline value of the metric. For example, during vestibular-ocular reflex function testing, and/or during remedial training, feedback is presented to the subject by displaying a circle or other feedback object (e.g., using display 308 or feedback device 208, FIG. 3) surrounding or nearby the object being visually tracked by the subject, and the color and/or size of the feedback object are dynamically changed to indicate the quality of the subject's performance. In a more specific example, the size of the feedback object may decrease when the subject's performance improves, shrinking to a predefined size when the subject's performance meets predefined criteria, and may increase when the subject's performance worsens. In some embodiments, system 300 varies the size of the feedback object based on (e.g., a predefined function of) the difference between a measurement metric (e.g., the variability or standard deviation of eye position error, such as horizontal eye position error or vertical eye position error, depending on the direction or movement of the subject's head during the vestibular-ocular reflex function testing) and a target value or baseline value of the metric. Alternatively, or in addition, system 300 varies the color of the feedback object, or the color of the object being tracked, or the color of a displayed background that forms a background for the object being tracked, based on (e.g., a predefined function of) the difference between a measurement metric (e.g., the variability or standard deviation of eye position error, such as horizontal eye position error or vertical eye position error, depending on the direction or movement of the subject's head during the vestibular-ocular reflex function testing) and a target value or baseline value of the metric.

Such remedial training exercises portions of the subject's brain that are responsible for cognitive tasks associated with anticipating events. By focusing the training narrowly on those cognitive tasks associated with anticipating events, appropriate portions of the brain are stimulated, which causes the brain to find ways to improve the subject's ability to anticipate the timing of predictable events. In some embodiments, only positive feedback signals are generated, to reward performance meeting predefined or individually determined performance goals. In other embodiments, the feedback signals include negative feedback signals that indicate failure to meet the performance goals. In still other embodiments the feedback signals may include gradations to indicate the extent to which the subject has met or failed to meet the performance goals.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

It will be understood that, although the terms "first," "second," etc. may be used herein to describe various elements, these elements should not be limited by these terms. These terms are only used to distinguish one element from another. For example, a first sound detector could be termed a second sound detector, and, similarly, a second sound detector could be termed a first sound detector, without changing the meaning of the description, so long as all occurrences of the "first sound detector" are renamed consistently and all occurrences of the "second sound detector" are renamed consistently. The first sound detector and the second sound detector are both sound detectors, but they are not the same sound detector.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "upon a determination that" or "in response to determining" or "in accordance with a determination" or "upon detecting" or "in response to detecting" that the stated condition precedent is true, depending on the context.

What is claimed is:

1. A system of testing and training a subject, comprising:
an eye gaze position measurement apparatus;
a head position measurement apparatus;
a computer control system coupled with the eye gaze position measurement apparatus and the head position measurement apparatus, the computer control system comprising one or more processors, and memory storing one or more programs, the one or more programs comprising instructions to:
present the subject with a display of an object;
verify that the subject's head is moving horizontally or vertically within a predefined range of movement rates;
while presenting the display of the object to the subject and verifying that the subject's head is moving horizontally or vertically within the predefined range of movement rates:
measure, using the head position measurement apparatus, the subject's head position; and
measure, using the eye gaze position measurement apparatus, the subject's right eye gaze positions or the subject's left eye gaze positions;
generate a metric representative of the subject's vestibular-ocular reflex function by statistical analysis of the measurements of subject's right eye gaze positions or the subject's left eye gaze positions, wherein the generated metric corresponds to a standard deviation, or variability, of error in the subject's eye gaze position, relative to the position of the displayed object; and
generate a report based on the metric, including presenting feedback to the subject, in accordance with the metric, while continuing to present the object to the subject and while the subject's head continues to move horizontally or vertically within the predefined range of movement rates, so as to train the subject to improve the subject's cognitive or oculomotor performance.

2. The system of claim 1, wherein the displayed object is stationary during said measuring of the subject's right eye gaze positions or the subject's left eye gaze positions.

3. The system of claim 1, wherein the object is a displayed object that moves in a repeating pattern during said measuring of the subject's right eye gaze positions or the subject's left eye gaze positions.

4. The system of claim 1, wherein the object is a displayed object that moves in a manner synchronized with and in a same direction as movements of the subject's head during said measuring of the subject's right eye gaze positions or the subject's left eye gaze positions.

5. The system of claim 1, wherein presenting the feedback to the subject includes varying an aspect of the feedback in accordance with a difference between the metric and a target value or baseline value of the metric.

6. The system of claim 5, wherein varying the aspect of the feedback includes varying a size or color of a presented feedback object in accordance with the difference between the metric and the target value or the baseline value of the metric.

7. A system of testing a subject for impairment, comprising:
an eye gaze position measurement apparatus;
a head position measurement apparatus;
a computer control system coupled with the eye gaze position measurement apparatus and the head position measurement apparatus, the computer control system comprising one or more processors, and memory storing one or more programs, the one or more programs comprising instructions to:
present the subject with a display of an object;
verify that the subject's head is moving horizontally or vertically within a predefined range of movement rates, wherein the predefined range of movement rates is 0.1 to 1 Hz;
while presenting the display of the object to the subject and verifying that the subject's head is moving horizontally or vertically within the predefined range of movement rates:
measure, using the head position measurement apparatus, the subject's head position; and
measure, using the eye gaze position measurement apparatus, the subject's right eye gaze positions or the subject's left eye gaze positions;
generate a metric representative of the subject's vestibular-ocular reflex function by statistical analysis of the measurements of subject's right eye gaze positions or the subject's left eye gaze positions, wherein the generated metric corresponds to a standard deviation, or variability, of error in the subject's eye gaze position, relative to the position of the displayed object; and
generate a report based on the metric.

8. A system of testing and training a subject, comprising:
an eye gaze position measurement apparatus;
a head position measurement apparatus;
a computer control system coupled with the eye gaze position measurement apparatus and the head position measurement apparatus, the computer control system comprising one or more processors, and memory storing one or more programs, the one or more programs comprising instructions to:
present the subject with a display of a stationary object;
while presenting the display of the stationary object to the subject, and the subject's head moves horizontally or vertically within a predefined range of movement rates:
measure, using the head position measurement apparatus, the subject's head position; and measure, using the eye gaze position measurement apparatus, the subject's right eye gaze positions or the subject's left eye gaze positions;

generate a metric representative of the subject's vestibular-ocular reflex function by statistical analysis of the measurements of subject's right eye gaze positions or the subject's left eye gaze positions, wherein the generated metric corresponds to a standard deviation, or variability, of error in the subject's eye gaze position, relative to the position of the displayed object; and generate a report based on the metric, including presenting feedback to the subject, in accordance with the metric, while continuing to present the object to the subject and while the subject's head continues to move horizontally or vertically within the predefined range of movement rates, so as to train the subject to improve the subject's cognitive or oculomotor performance.

9. A system of testing a subject for impairment, comprising:
an eye gaze position measurement apparatus;
a head position measurement apparatus;
a computer control system coupled with the eye gaze position measurement apparatus and the head position measurement apparatus, the computer control system comprising one or more processors, and memory storing one or more programs, the one or more programs comprising instructions to:

present the subject with a display of a stationary object;

while presenting the display of the stationary object to the subject, and the subject's head moves horizontally or vertically within a predefined range of movement rates, wherein the predefined range of movement rates is 0.1 to 1 Hz measure, using the head position measurement apparatus, the subject's head position; and measure, using the eye gaze position measurement apparatus, the subject's right eye gaze positions or the subject's left eye gaze positions;

generate a metric representative of the subject's vestibular-ocular reflex function by statistical analysis of the measurements of subject's right eye gaze positions or the subject's left eye gaze positions, wherein the generated metric corresponds to a standard deviation, or variability, of error in the subject's eye gaze position, relative to the position of the displayed object; and generate a report based on the metric.

* * * * *